United States Patent [19]

Huebsch

[11] Patent Number: 4,892,550

[45] Date of Patent: Jan. 9, 1990

[54] ENDOPROSTHESIS DEVICE AND METHOD

[76] Inventor: Donald L. Huebsch, 3716 Prestwick Dr., Los Angeles, Calif. 90027

[21] Appl. No.: 814,690

[22] Filed: Dec. 30, 1985

[51] Int. Cl.$^4$ .............................................. A61F 2/32
[52] U.S. Cl. ........................................... 623/22; 623/16
[58] Field of Search ................. 128/92 R; 623/14, 16, 623/20, 23, 22

[56] References Cited

U.S. PATENT DOCUMENTS

| | | | |
|---|---|---|---|
| 4,399,814 | 8/1983 | Pratt et al. | 128/92 R |
| 4,562,598 | 1/1986 | Kranz | 623/20 |

Primary Examiner—Richard J. Apley
Assistant Examiner—James Prizant
Attorney, Agent, or Firm—Christie, Parker & Hale

[57] ABSTRACT

Disclosed is an endoprosthesis device and method of installing the same immovably in a medullary canal under a constant predetermined uniformly distributed pressure. The rigid prosthesis stem is typically embraced by an elastomeric element designed for continuous pressurization into compressed resilient anchorage with the medullary canal surface. The tubular elastomeric element can be pressurized in various ways such as by a captive gas, or by a fluent material until this material takes a set, or by a combination of pressurized gas and settable fluent material. When a captive pressurized gas is used, along or with a settable material, it provides a major portion of the elastic energy anchoring the prosthesis immovably in place; and when a settable pressurizing medium is used, the elastic energy is stored in the compressed thick elastomer. The constant elastic energy fosters bone growth to augment prosthesis anchorage. Permanent anchorage is achieved virtually instantly following alignment and pressurization of the prosthesis. When a settable material is used, the stem may include a withdrawable wedge to facilitate separation of the remainder of the prosthesis from the medullary canal. The expandable/compressible elastic component readily compensates for irregularity in the canal wall and requires a minimum of preliminary preparation of its surface.

37 Claims, 4 Drawing Sheets

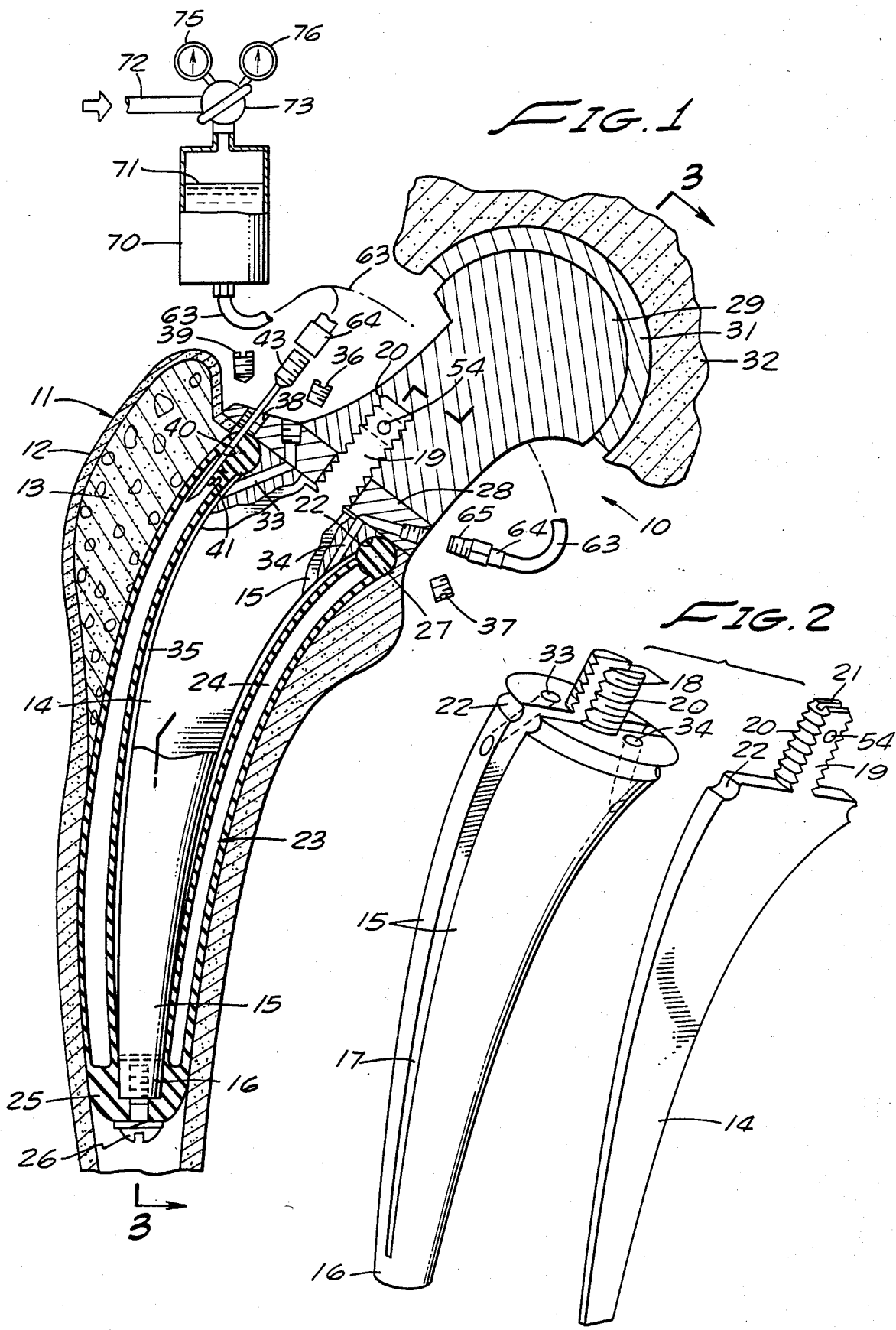

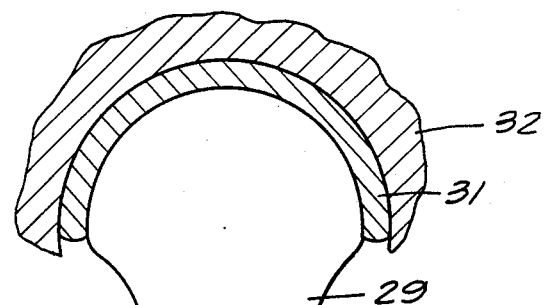
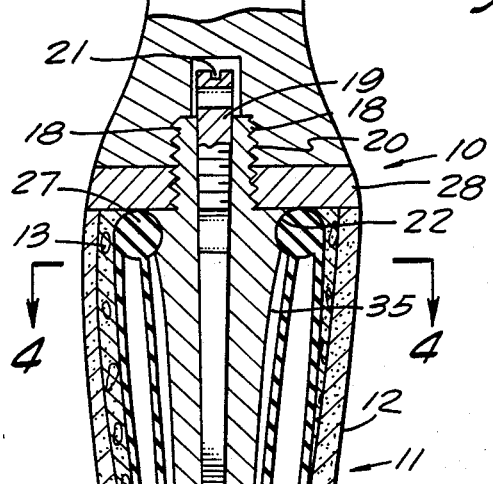
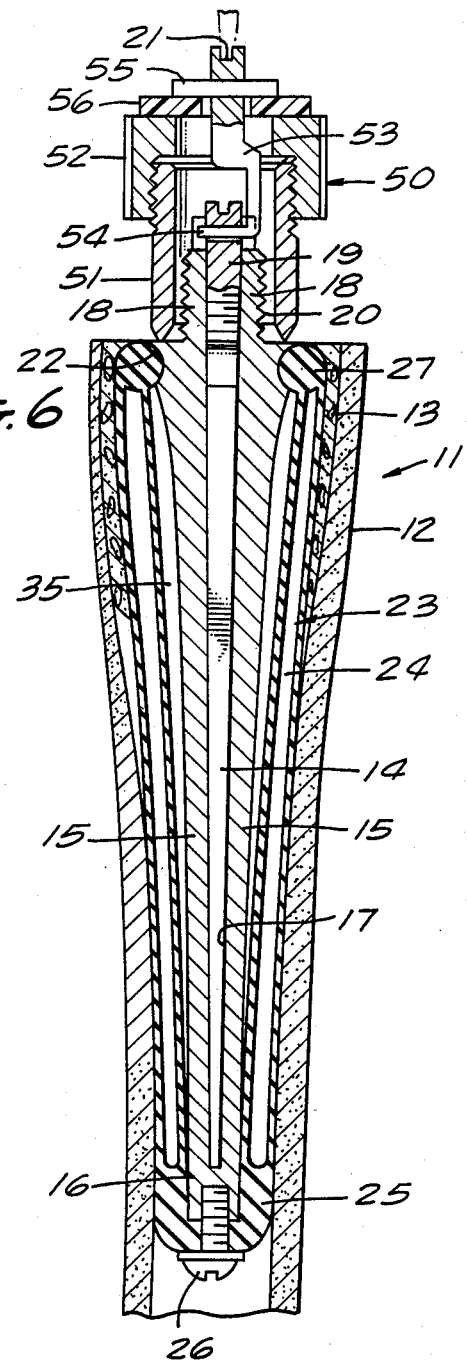
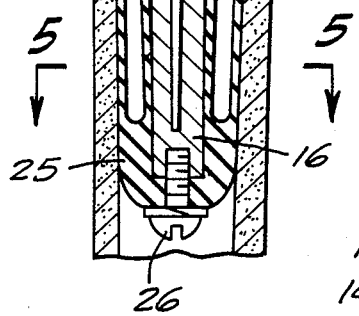
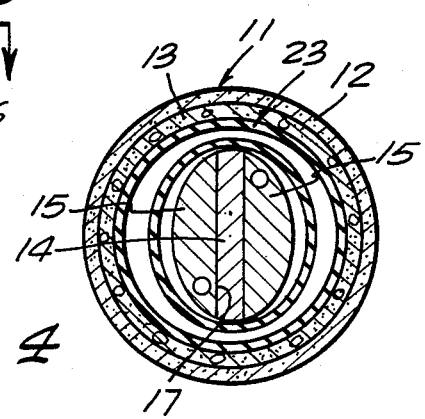
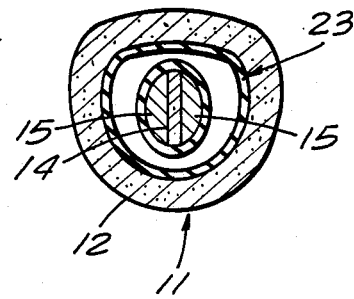

ENDOPROSTHESIS DEVICE AND METHOD

BACKGROUND OF THE INVENTION

The provision of an endoprosthesis that provides immediate and long term functional reliability continues to be one of the critical objectives in orthopedic research. The typically critical aspect has been the inability to provide a simple easily installed trouble free anchorage to the medullary canal and the ability to remove the prosthesis without damaging the bone. Many techniques, structures and operating principles have been proposed heretofore conveniently characterized as (1) a stem impacted into the medullary canal; (2) a stem fixed mechanically in situ by screws, pins, expansion mechanisms or the like; (3) a stem fixed by cement, (4) a porous stem gradually and eventually anchored by bone growth into the stem voids; and (5) stems equipped with one or more resilient anchorage expedients.

Each of these prior proposals is subject to shortcomings and disadvantages. Illustrative embodiments of certain of these proposals are in the following U.S. Pat. Nos., viz; Fischer 3,846,846; Rostoker 3,906,550; Kahn 3,938,198; Rybicki et al 4,011,602; Rosenberg 4,013,071; Bokros 4,038,703; Pifferi 4,051,559; Berner et al 4,124,026; Grundel et al 4,167,047; Grell et al 4,177,524; Koeneman 4,292,697; and Koeneman 4,314,381.

Each of these methods presents problems that can lead to failure of the arthroplasty. The problems are as follows:

In devices that are impacted into the bone canal or held in place by expansion bolts or bone screws bearing against surrounding bone, the actual surface of contact between the prosthesis and the bone may be very small and areas of stress concentration will frequently occur. Clinical observations report loosening of the implant due principally to bone resorption.

Devices requiring the use of cement for anchorage are subject to problems associated with the toxicity of the cement, necrosis of the adjacent bone, incomplete filling of the desired intramedullary space, and the absence of resiliency. In addition, reports of long-term results of cemented total hip replacements with a minimum follow-up of ten years indicate that the loosing rate on the femoral side ranges between 30 to 50 percent.

Stem emplacements relying on bony ingrowth for attachment of the stem to the bone canal wall require excellent apposition of the stem. Typically a gap of one millimeter will exceed the growth capacity of the bone. In addition, if motion prior to fixation should occur, fibrous tissue results rather than new bone growth.

Prior proposals for resilient anchorages involve various expedients utilizing coil springs having portions of their convolutions in contact with the bone or strips of resilient material mounted on a supporting prosthesis stem and providing resilient backing for rigid elements in contact with the bone cavity. All have limited contact with the bone and lack provision for uniformly distributed equalized pressure in a controlled predetermined amount to substantially all portions of the bone cavity opposite the body of the prosthesis.

SUMMARY OF THE INVENTION

The present invention obviates the shortcomings and disadvantages of prior proposals for an endoprosthesis by the provision of a unique simplified assembly, readily and freely insertable into the medullary canal following a minimum of preparatory operations and featuring elastic means compressible into high pressure resilient contact with the canal surface. Toxicity and necrosis is avoided by utilizing a biocompatible elastomer in direct contact with the canal bone tissue. The elastomer automatically compensates for irregularities in the shape and size of the canal and if the inside of the canal is substantially fully contacted by elastomer as is preferred, all portions of the canal in juxtaposition to the outer surface of the elastomer are placed under uniformly distributed pressure of a desired predetermined magnitude. Expansion of the pressurized elastomer into the natural canal irregularities rigidly anchors the prosthesis against both axial and rotary movement. In an illustrative embodiment, the elastomer comprises a tubular double walled bladder loosely embracing the stem of the prosthesis and having its opposite ends secured to the stem with provision for introducing a pressurizable medium into the bladder, or additionally between the stem and its inner wall, or into both of these chambers, serves to expand the elastomer and to hold major portions thereof elastically compressed against the canal surface. These elastic pressures can be maintained indefinitely by sealing the pressurized cavity or cavities. Moreover, these predetermined high pressures are distributed uniformly and are highly effective in fostering and promoting invigorated bone growth thereby further increasing the elastic pressure and augmenting its anchorage to the prosthesis.

Various mediums may be utilized to pressurize the prosthesis including either gaseous medium, or an initially fluid medium which takes a rigid set preferably an exothermic epoxy compound and which is maintained pressurized while setting occurs whereby the elastomer remains permanently compressed against the canal wall, or a combination of gaseous and settable mediums. When gas alone is the pressurizing medium, thinner elastomer can be employed because the pressurized gas is a highly elastic medium.

If circumstances should arise wherein it is desirable for some reason to remove the prosthesis, provision is made in all embodiments for this purpose. If the elastomer is maintained pressurized by either a gaseous medium or by a combination of a gaseous and a settable medium, prosthesis removal is easily and quickly achieved by venting the gaseous pressurizing medium. If only a settable pressurizing medium is utilized, prosthesis removal can be aided by providing the stem with a withdrawable wedge centrally of the stem thereby permitting the remaining portions to collapse toward one another to achieve separation from the canal wall. If a friable setting medium is employed this is readily shattered by collapse of the stem and the application of impact and shock forces to the friable material.

Accordingly, it is a primary object of this invention to provide an improved simplified endoprosthesis and method of anchoring the same in a medullary canal with provision for maintaining it indefinitely and immovably therein.

Another object of the invention is the provision of an endoprosthesis wherein the stem is embraced by an elastomer provided with a cavity chargeable with a pressurizing medium after insertion and precise positioning of the prosthesis.

Another object of the invention is the provision of an endoprosthesis having a stem supporting an elastomeric ring and provided with means for compressing the ring into uniformly distributed pressurized contact with the medullary canal.

Another object of the invention is the provision of a novel method of implanting a prosthesis in a medullary canal wherein the prosthesis can be freely moved and precisely aligned with contiguous skeletal components and then immovably anchored in place under predetermined uniformly distributed pressure.

Another object of the invention is the provision of an endoprosthesis having a rigid stem embraced by an elastomeric member secured to its opposite end portions and adapted to be expanded against the surface of the medullary canal under uniformly distributed pressure to foster invigorated bone growth including growth into surface irregularities of the elastomeric tube.

Another object of the invention is the provision of endoprosthesis having a pressurizable cavity including an elastomeric outer wall compressed into uniformly distributed contact with a medullary canal irrespective of irregularities in the shape and size of the canal.

Another object of the invention is the provision of an endoprosthesis anchored immovably in a resilient interface with the medullary canal.

Another object of the invention is the provision of an installed endoprosthesis which is collapsible inwardly following axial withdrawal of a member extending longitudinally thereof.

Another object of the invention is the provision of an endoprosthesis having a nontoxic, nonmetallic uniformly pressurized resilient interface with living bone tissue.

Another object of the invention is the provision of endoprosthesis having a permanent compatible resilient elastomeric interface with living bone tissue.

Another object of the invention is the provision of a prosthesis utilizing a stem of noncircular cross section embraced by elastomer held compressed against irregularities in a medullary canal by an initially fluent pressurized settable medium to anchor the prosthesis against rotary movement.

Another object of the invention is the provision of a prosthesis utilizing a rigidly settable pressurizing medium retained captive within an elastomeric envelope effective as a heat barrier between bone tissue and exothermic curing heat of the settable medium.

Another object of the invention is the provision of an endoprosthesis selectively anchorable immovably in place under uniformly distributed pressure by pressurized gas, or by a settable medium, or by a combination of both retained captive in separable chambers.

Another object of the invention is the provision of an endoprosthesis and method utilizing a plurality of separate concentric cavities each including at least one elastomeric wall and an outer one of which cavities is initially chargeable with gas under low pressure and an inner one of which cavities is chargeable with a pressurized medium effective to hold the outermost wall resiliently compressed against a medullary canal.

These and other more specific objects will appear upon reading the following specification and claims and upon considering in connection therewith the attached drawing to which they relate.

Referring now to the drawing in which preferred embodiments of the invention is illustrated:

FIG. 1 is a longitudinal cross sectional view through a first illustrative embodiment of the invention together with apparatus for charging the chambers thereof with pressurizing mediums but prior to the charging operation;

FIG. 2 is an exploded view of the stem portion of the prosthesis shown in FIG. 1;

FIG. 3 is a cross sectional view taken along the broken line 3—3 on FIG. 1;

FIG. 4 is a cross sectional view taken along line 4—4 on FIG. 3;

FIG. 5 is a cross sectional view taken along line 5—5 on FIG. 3;

FIG. 6 is a cross sectional view similar to FIG. 3 but showing the head detached and the wedge puller assembled to the wedge and in readiness for use to retract the wedge;

Figure 8:
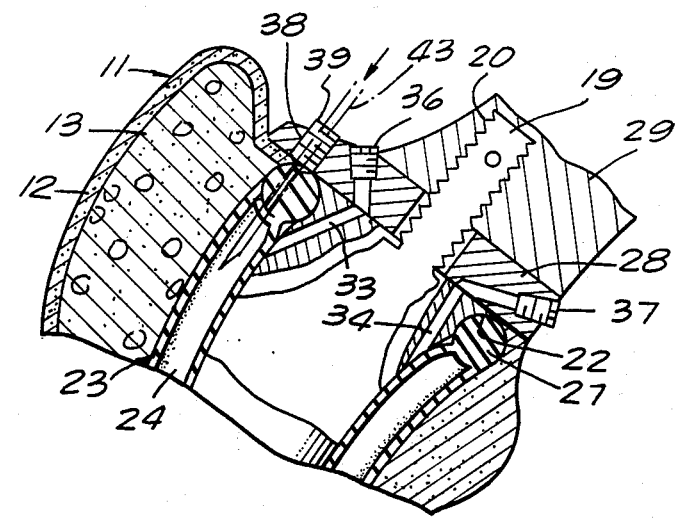
FIG. 8 is a fragmentary cross sectional view of the upper portion of FIG. 1 showing the bladder pressurized solely by a gaseous medium.
Figure 9:
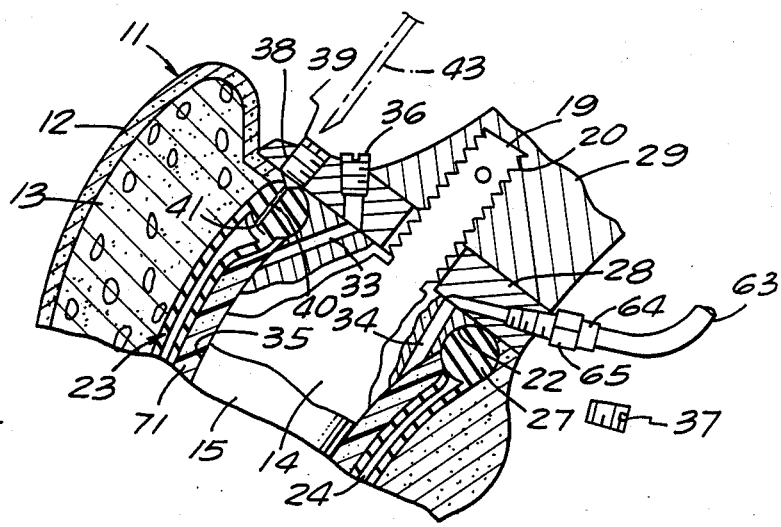
FIG. 9 is a fragmentary cross sectional view of the upper portion of FIG. 1 showing a gas charge in the bladder and a charge of a pressurized settable medium between the stem and the inner bladder wall.
Figure 10:
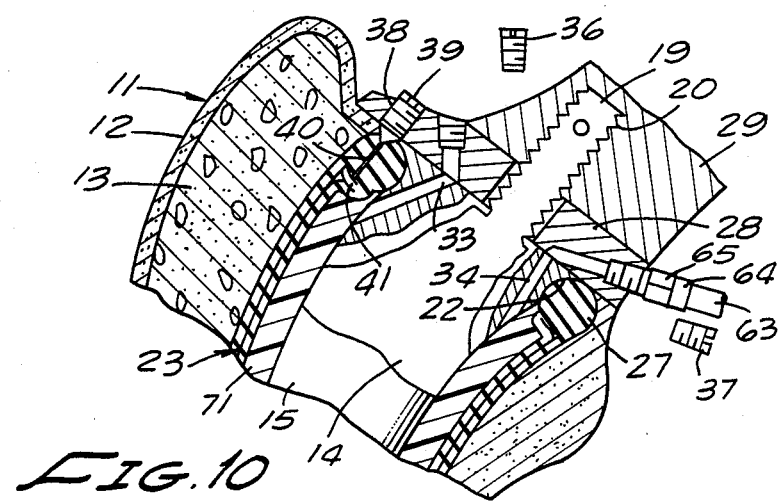
Figure 11:
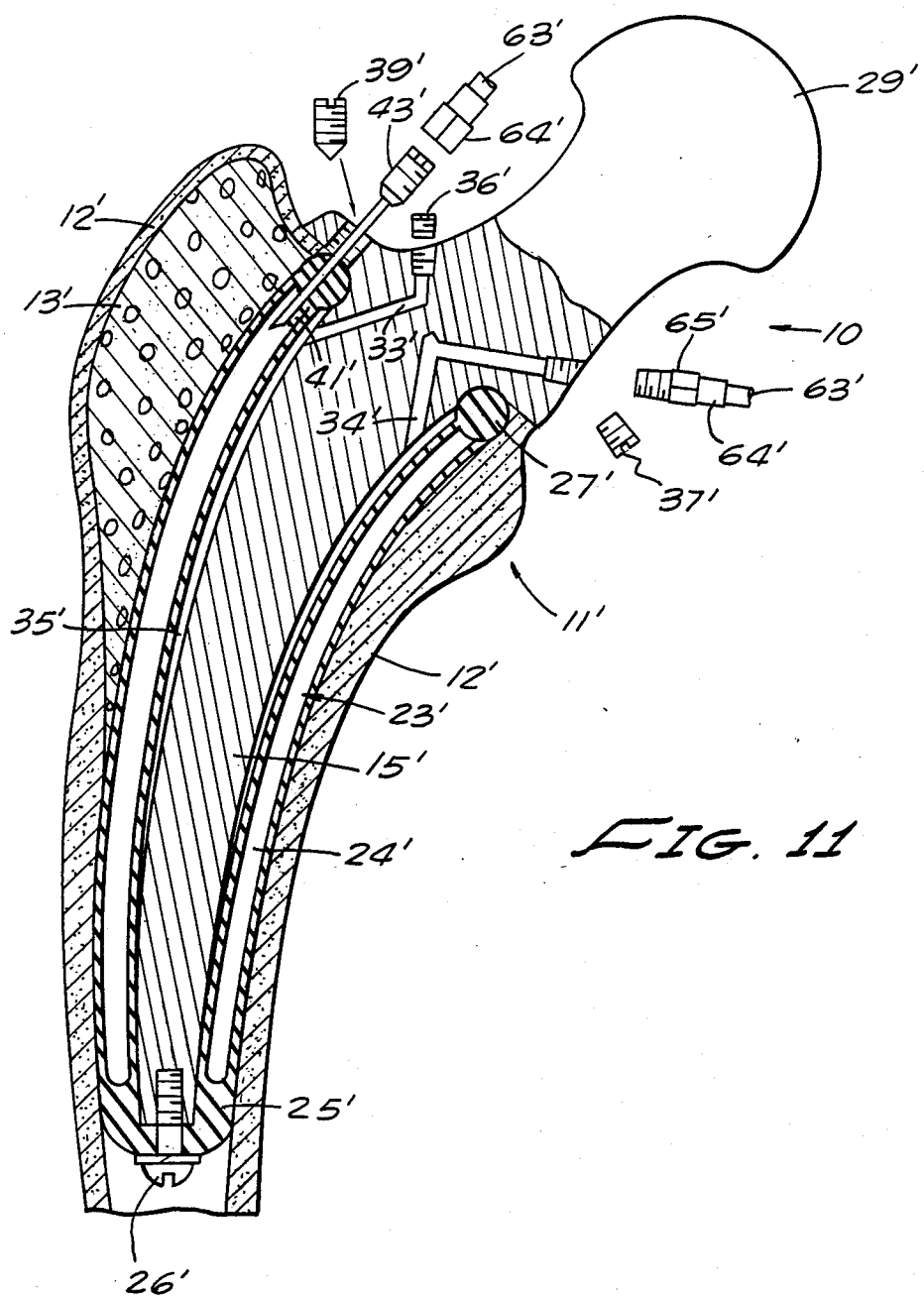

FIG. 10 is a fragmentary cross sectional view of the upper portion of FIG. 1 showing a pressurized charge of a settable medium between the stem and the bladder and holding both bladder walls resiliently pressed together with the outer wall pressed against the medullary canal; and FIG. 11 is a cross sectional view of a second preferred embodiment differing from the embodiment shown in FIGS. 1–10 in that it has a one piece stem and head.

Referring initially more particularly to FIGS. 1–10, there is shown a first illustrative embodiment of the invention prosthesis, designated generally 10, installed in the upper end of a femur bone 11 after the neck and head of that bone have been severed. The femur has a dense outer sheath 12 and a lining of spongy bone tissue 13. As shown, a portion of the surface of tissue 13 has been removed in accordance with customary practice to make room for the insertion of prosthesis 10.

The rigid metallic stem of the prosthesis is best shown in FIG. 2 and includes a central wedge member 14 insertable between two generally semicircular elliptical members 15, 15 interconnected at the inner smaller end 16 and separated by a slot 17 having sidewalls diverging upwardly similarly to the taper of wedge member 14. Members 14 and 15 are provided with axial extensions 18 and 19 centrally of their upper ends and each provided with threads 20 which register with one another to form a continuous spiral thread matable with other threaded components of the assembly to be described presently. Extension 19 includes a tool seating slot 21 across its upper end. The larger outer ends of stem members 14, 15 are encircled with a groove 22 of semicircular cross section firmly seating the inlet end of an elastomeric member to be described presently.

Stem members 14, 15 are embraced by a thick walled biocompatible elastomeric bladder 23 having an annular cavity 24, the inner wall of which cooperates with the stem elements 14 15 in forming the cavity 35. Various elastomers which are nontoxic to live bone tissue may be used including surgical rubbers and plastics, vinyl being a particularly suitable example of many suitable elastomers. Various wall thicknesses provide excellent results, thinner walls being adequate when using a gaseous pressurizing medium and thicker walls being desirable for nongaseous and solid pressurizing charges for the cavity between the stem proper and the elastomeric wall. Wall thicknesses of ⅛" to 1/16" provide excellent results.

Provision is made for securing the opposite ends of bladder 23 to the adjacent end portions of the stem. As herein shown, the inner smaller end 25 is thicker and snugly embraces the lower end of stem members 15, 15 to which the elastomer is secured in a fluid tight manner by the threaded fastener 26. The outer larger end of the bladder includes a thick walled ringlet 27 having a fluid tight seat in groove 22 of the stem members. As is best shown in FIGS. 4 and 5, the assembled stem members 14 and 15 are preferably elliptically shaped with the longer axis of the ellipse lying in a plane transversely of the femur as viewed in FIG. 1. The dual purposes served by this elliptical configuration will be explained presently.

Detachably assembled to the threaded projections 18 and 19 of the stem members is a thin relatively large diameter nut 28 and a head element 29 contoured and shaped to replace the detached head and neck of the femur. Head 29 is seated in an acetabular cup 31 in the pelvis 32. Stem members 15 and nut 28 are provided with two pairs of passages 33 and 34 which are in registry with one another when nut 28 is fully tightened on the threaded projections 18 and 19. Both passages communicate with the pressurizable cavity 35 between the stem and the inner wall of the bladder 23 and their outer ends are normally closed by gasketed plugs 36, 37. One of the passages 33, 34 serves to vent cavity 35 during the charging operation and the other as a charging passage for a pressurizing medium. Nut 28 is also provided with a threaded passage 38 normally closed by a gasketed plug 39. Passage 38 is in alignment with a passage 40 through the underlying bladder ringlet 27. The inner end of passage 40 is provided with a suitable resilient, normally closed, valve such as the valve flap 41 or a conventional duck bill valve well known to persons skilled in the construction of inflatable bladders for sporting goods. Such valves open to receive a bladder charging device such as a hypodermic needle 43 and reclose automatically upon its withdrawal.

Attention is called to FIGS. 4 and 5 taken at different axial distances along the prosthesis. To be noted is the fact that the medullary canal is typically naturally irregularly contoured and sized differently at different transverse locations therealong. Thus FIG. 4 represents a typical cross sectional view of the canal near its entrance end wherein both the bone shell and the inner surface of the canal are generally circular. In other transverse planes both the bone shell and the inner surface of the canal may and usually do vary in shape in a pronounced degree from circular. Thus, in the plane indicated in FIG. 5, both the shell and the canal wall are roughly triangular in cross section and so oriented that the elliptically shaped stem elements 14 and 15 are disposed as indicated in FIG. 5. An important aspect of the present invention resides in the fact that despite these customary and typical irregularities, the construction and operating principles of the prosthesis bladder automatically, reliably and completely compensate for these irregularities. Moreover, the expansion of the bladder into these irregularities and into conformity with the curvate stem anchors the prosthesis immovably in place and against all rotary or longitudinal movement. Rotary movement is also safeguarded by making the stem elliptical in cross section. These features characterizing this invention avoid the need for extensive and time consuming contouring of the canal surface and assure that substantially the entire length of the embraced portion of the prosthesis will be in predetermined uniform pressure contact with live bone tissue.

Referring to FIG. 6 there is shown a puller assembly 50 usable to remove the prosthesis should this ever become desirable for any reason when the inner bladder cavity 35 is charged with a pressurized exothermic medium such as epoxy or plaster of Paris. Removal is accomplished by detaching the head 29. Then a screw driver is inserted in the slot 21 at the outer end of extension 19 while a second tool is employed to unscrew nut 28 from the threaded projections 18 and 19 at the outer ends of stem members 14 and 15. A puller assembly, designated generally 50, comprising the elements shown at the top of FIG. 6 are then assembled astride the projections 18 and 19. The puller includes a short bifurcated sleeve 51, a threaded bushing 52 assembled to its threaded upper end and a J-shaped puller member 53 having the hook at its lower end seated in a hole 54 extending across the upper end of the wedge member 14. A pin 55 extends through the upper end of the stem portion of puller 53 and is seated on a washer 56 resting on bushing 52. The bifurcated lower end of sleeve 51 straddles projections 18 and 19 and bears against the tops of the two stem members 15 resting against the opposite sides of wedge 14.

Figure 7:
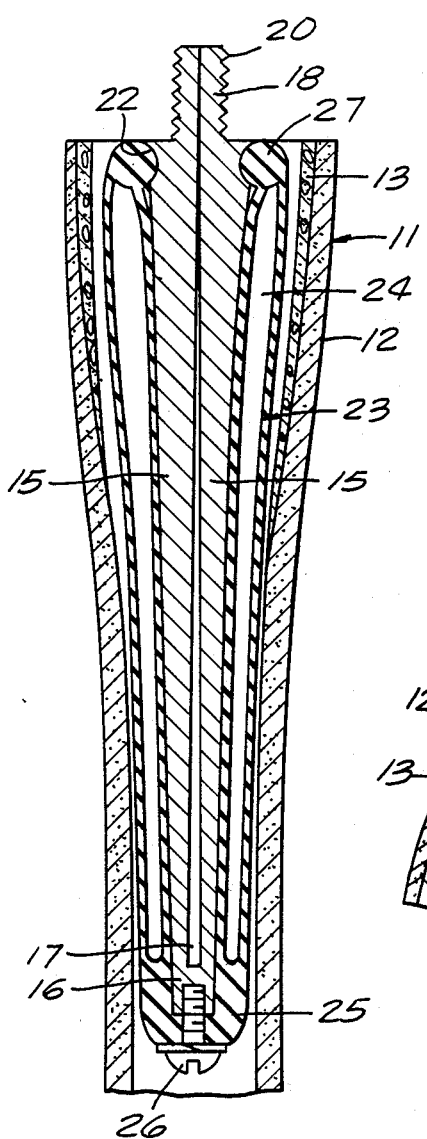
FIG. 7 is a view similar to FIG. 6 but showing the wedge detached and the remaining components of the stem collapsed together to separate the prosthesis from the medullary canal.

When bushing 52 is rotated to move upwardly along the threads of sleeve 51 it will be evident that the hook member 53 acts to withdraw the wedge. Only a relatively short lifting movement is required to release the wedge from between stem members 15, 15 along with the puller assembly 50. Thereafter, pliers or the like are applied to the threaded projections 19 forcing these members to collapse members 15, 15 inwardly against one another as shown in FIG. 7 releasing the elastic bladder 23 from the live bone tissue. The portion of the rigid epoxy or plaster of Paris material in the innermost chamber 35 of the bladder opposite the longer axis of the elliptical stem elements is relatively thin and fractures as the stem members are forcibly collapsed against one another. The elliptical shape of the stem in addition to aiding fracture of the rigid material during removal of the prosthesis also normally serves to prevent rotation within the bladder.

Another illustrative embodiment of the invention is shown in FIG. 11 wherein the same or similar elements are designated by the same reference characters as in the first described embodiment but distinguished therefrom by the addition of a prime. Embodiment 10' differs structurally from the first embodiment in that it has an integral one piece head and stem, preferably of elliptical or non-circular cross section, made from suitable material well known to persons skilled in this art.

INSTALLATION AND USE

Both embodiments can be installed and pressurized in one of several modes. The head of the damaged femur is severed along a transverse plane as indicated in FIG. 1 and a portion of the spongy bone tissue 13 is removed from the medullary cavity to the extent necessary to admit the prosthesis 10, it being apparent that the elastomeric component is very flexible and inherently adapted to accommodate itself to irregularities in the cavity wall. The prosthesis bladder 23 is preferably evacuated as made or before installation and occupies a minimum of space adjacent the prosthesis stem. Accordingly, the fully assembled prosthesis is readily inserted as a unit with the base of the head lying flush against the prepared flat end of the femur.

FIG. 1 shows suitable equipment for pressurizing the interior of bladder 23 or the space 35 between the stem and the inner wall of the bladder in any selected one of the several optional pressurizing modes. This equipment comprises a container 70 chargeable with an initially fluent exothermic medium compounded to take a rigid set within a short period, such as epoxy or plaster of Paris 71. The top of this container can be pressurized with gas from a suitable source at several hundred psi via a conduit 72 connected to a flow control valve 73 having a pair of pressure gauges 75, 76. Gauge 75 indicates the pressure of the gas source and gauge 76 indicates the pressure acting on medium 71 in container 70.

The bottom of the pressurizing medium container 70 is equipped with a flexible hose 63 having a threaded fitting 64 on its outlet end. Fitting 64 can be connected either to the threaded shank of a hypodermic needle 43 or to a fitting 65 mateable with the threaded inlet of passage 34 leading into the space 35 between the prosthesis stem and the inner wall of bladder 23 depending upon whether the interior of the bladder is to be pressurized with the exothermic medium 71 or whether the space 35 between the stem and the inner wall of the bladder is to be charged with this medium. If medium 71 is not to be charged into either cavity, then container 70 is utilized empty and control valve 73 is utilized to pressurize the bladder as will be explained in detail presently.

Pressurization of the bladder of either embodiment will be described with reference to FIGS. 1 and 8. The prosthesis including its evacuated bladder is inserted into the prepared medullary cavity and is accurately aligned with the femur and the acetabular cup 31 of the bone 32. Plugs 36, 37 and 39 are removed to vent any air from between the stem and the inner wall of the bladder and to permit insertion of the hypodermic needle 43 through passage 40 in the thickened rim 27 at the upper end of the bladder thereby opening the normally closed valve 41. Coupling 64 of hose 63 is assembled to the hypodermic needle prior to the insertion of the needle into the bladder and valve 73 of the charging apparatus is thereafter manipulated to charge the bladder cavity 24 with a suitable rigidly settable material such as epoxy or plaster of Paris 71 to a desired pressure, such as 350 psi or any other superatmospheric value chosen by the surgeon as desirable. Pressures between 200 and 450 psi are suitable but a lower pressure may be selected. As previously stated, cavity 24 is evacuated eliminating the need for venting cavity 24. During the charging operation any air present in cavity 35 is vented to the atmosphere through passages 33 and 34 following which these passages are sealed closed by plugs 36, 37. Any air between the bladder outer wall and the medullary canal bone wall will be vented out between the bone and ringlet 27. When the bladder is fully charged its walls are pressed against the medullary cavity and against the prosthesis stem and maintained at the preselected pressure while the charging medium takes a rigid set. Thereafter the hypodermic needle 43 is withdrawn and plug 39 is reseated.

The thick walls of the bladder are now compressed under the preselected pressure against and in conformity with all juxtaposed areas of the medullary cavity throughout substantially the full length of the stem thereby anchoring the prosthesis immovably in place under this uniformly distributed predetermined elastic pressure.

In a second optional mode of anchoring either embodiment of the prosthesis immovably in place, the bladder cavity is charged with pressurized gas. This operation is carried out by coupling the shank of a hypodermic needle 43 to the coupling 64 of hose 63, container 70 being empty (FIG. 1). Thereafter the hypodermic needle is inserted through passage 40 at the upper end of the bladder after the closure plugs 36, 37 and 39 have been removed. Valve 73 is then opened to admit pressurized gas from source conduit 72 to a desired pressure indicated by gauge 76. Any air present in cavity 35 between the bladder and the stem is vented to the atmosphere via passages 33 and 34. The charging operation is not performed until the surgeon has taken due care to ascertain that the femur is properly aligned in the acetabular cup 31 of bone 32. When charging to a desired pressure has been attained as indicated by gauge 76, needle 43 is withdrawn as valve 41 closes automatically trapping the charged air in the bladder. Plug 39 is immediately reseated in threaded bore 38 to further seal the charge captive within the bladder. Also plugs 36 and 37 are reinstalled. The elastic pressure stored in the outer wall of the bladder is now augmented by the elastic characteristics of the pressurized gas charge in the bladder.

Still another charging option and mode is illustrated in FIG. 9 wherein the evacuated bladder of either embodiment is inflated with gas at low pressure such as one atmosphere and is accomplished by the pressurized gas technique just described. Thereafter this trapped small quantity of gas can be pressurized to high elastic pressure by charging the exothermic medium 71 into the cavity 35 between the stem and the inner wall of bladder 23. This charging mode is carried out with the charging apparatus shown in FIG. 1 connected to the prosthesis as will now be described in connection with FIG. 9. Plugs 36, 37 are detached. Plug 39 has been reseated with low pressure gas in cavity 24. Hose 63 and its fitting 65 is connected to the inlet passage 34. The surgeon then accurately and precisely aligns the prosthesis with the femur and bone 32 and proceeds to admit pressurized epoxy or plaster of Paris from container 70 into the cavity 35 between the stem and the inner wall of bladder 23. Any air present in this cavity is vented to the atmosphere via the open passageway 33 after which plugs 36 is reseated. Pressurized epoxy is admitted under pressure by opening valve 73 until the pressure of the filled cavity reaches a desired value as indicated by pressure gauge 76. As the fluent exothermic medium 71 fills the cavity between the stem and the bladder wall, the small volume of captive gas in the bladder cavity 24 becomes pressurized to the same magnitude as the medium 71 in cavity 35. The inner and outer walls of the bladder are now nearly in contact and this small volume of highly compressed and highly elastic captive body of gas augments the high elastic compression stresses stored in the bladder walls and cooperates to hold the outer bladder wall in uniformly distributed highly elastic contact with the wall of the medullary canal. It is important that the exothermic medium be maintained pressurized for the short period of time required for it to take a rigid set. Once that has taken place, valve 73 can be closed, the hose connection 65 can be detached and plug 37 can be reseated.

Another alternate charging mode is illustrated in FIG. 10 wherein both the inner and outer walls of the evacuated bladder 23 are held elastically compressed against the medullar canal by pressurized exothermic medium 71 from container 70. The charging and installation procedure is similar to that described immediately above with minor exceptions. Both plugs 36 and 37 are detached but plug 39 remains installed and in sealing engagement with the entrance to the passage 40 for the hypodermic needle through the thick upper rim 27 of the bladder the cavity 24 having been evacuated. Fitting 65 of the flexible hose 63 is installed in the inlet of passage 34 in communication with the cavity 35 between the prosthesis stem and the inner wall of bladder 23. After accurate alignment of the prosthesis between the femur 11 and the acetabular cup of bone 32 the operator opens valve 73 of the charging apparatus to admit the exothermic medium 71 into the cavity 35 between the stem and the bladder via passage 34. Any air present in this cavity is vented to the atmosphere via passage 33. As soon as all air is released and the chamber is charged with epoxy, plug 36 is installed to seal passage 33 closed and permit a desired pressure to be applied and maintained on the medium 71 until the medium takes a rigid set to hold both walls of the bladder pressed against one another and against the wall of the bone tissue 13. Hose 63 and its fitting 65 can then be detached and the passage 34 closed by its plug 37. The combined compression energy then stored in the two walls of the bladder are available to maintain the prosthesis resiliently and immovably anchored to the femur.

Removal of either prosthesis embodiment when the bladder contains a pressurized charge of air, is facilitated by detaching plug 39 and inserting a needle 43 through passage 40 to vent the air. If the prosthesis includes a charge of an exothermic medium alone or in combination with pressurized air, removal is facilitated by use of the accessory 50 shown in FIG. 6 as will now be described.

After gaining access to the installed prosthesis, the surgeon detaches head 29 while a clamping tool is applied to nut 28 to hold the prosthesis stem stationary. A suitable tool is then inserted in slot 21 across the exposed outer end of extension 18 of the wedge component of the stem to hold the stem against rotation while nut 28 is being unwrenched. The hooked end of the J-shaped puller 53 is then installed through hole 54 in extension 19 of the wedge 14 and this is followed by inserting the bifurcated threaded sleeve 51 and bushing 52 astride extensions 18 and 19 as shown in FIG. 6 and secured to the outer end of puller member 53 by means of a washer 56 and a cross pin 55 inserted crosswise of the puller.

The bifurcated lower end of sleeve 51 straddles extensions 18 and 19 and bears against the tops of the two stem members 15 resting against the opposite sides of wedge 14. When bushing 52 is rotated to move upwardly along the threads of sleeve 51 it will be evident that the puller 53 acts to withdraw the wedge. Only a relatively short lifting movement is required to release the wedge from between stem members 15, 15 along with the puller accessory 50. Thereafter, pliers or the like are applied to the threaded extensions 19 forcing members 15, 15 to collapse inwardly against one another as shown in FIG. 7 releasing the bladder 23 from the live bone tissue. The portion of the rigid epoxy or plaster of Paris material opposite the longer axis of the elliptical stem elements is relatively thin and fractures as the stem members are forcibly collapsed against one another.

Laboratory experiments have demonstrated that bone ingrowth is stimulated when bone is subjected to load stresses beginning at about 150 psi and tapering to little or no ingrowth at 750 psi with excellent ingrowth occurring in the 250 to 350 psi range. Pressures in this range uniformly distributed over a substantial length of the bone will promote a healthy and substantial strengthening of pressurized portions of the bone by promoting bone growth toward the elastomeric member 23 to enhance the existing rigid anchorage of that member to the bone cavity. Additionally stress levels of 150 to 350 psi between the bone and elastomeric member 23 will produce pushout stress of the stem in excess of that which the bone could normally be subjected to.

While the particular endoprosthesis device and method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim;

1. A pressurizable elastic endoprosthesis anchoring apparatus freely insertable into a medullary canal and thereafter immovably anchorable thereto comprising:
   an elongated load bearing stem;
   an elastic member mounted around and extending lengthwise of said stem; and
   means for compressing said elastic member radially outward into pressurized contact with the juxtaposed surface of the medullary canal after insertion therein;
   the elastic member being fluid impervious and having an internal cavity, and said means for compressing said elastic member including means for introducing a fluent medium under pressure into said cavity to expand said elastic member into pressurized contact with said surface of the medullary canal and to continuously maintain the elastic member compressed in resilient pressure contact with the medullary canal surface, said elastic member being effective to distribute elastic pressure substantially uniformly to the surface area of the medullary canal in contact therewith and to conform to irregularities present in the juxtaposed surface portion of the medullary canal, said uniformly distributed elastic pressure applied continuously by the elastic member to the medullary canal being effective to anchor said endoprosthesis immovably therein.

2. An endoprosthesis anchoring apparatus as defined in claim 1 characterized in that said means for compressing said elastic member includes means for introducing a pressurized fluent medium between said stem and said elastic member adapted to set rigidly and for maintaining the same pressurized while said fluent medium sets in a rigid condition thereby to maintain said elastic means elastically compressed and pressurized indefinitely.

3. An endoprosthesis anchoring apparatus as defined in claim 2 characterized in that a major portion of said stem is noncircular in cross section whereby said stem is nonrotatable relative to said rigid medium after said medium sets.

4. An endoprosthesis anchoring apparatus as defined in claim 2 characterized in that said pressurized fluent medium is effective to expand said elastic member into conformity with irregularities in the surface of a medullary canal while taking a rigid set thereby to anchor said stem immovably in place in said canal.

5. An endoprosthesis anchoring apparatus as defined in claim 2 characterized in that said fluent medium is readily friable in response to impact forces applied thereto in a manner to effect removal of the prosthesis if removal is desired.

6. An endoprosthesis anchoring apparatus as defined in claim 1 characterized in that said means for compressing said elastic member with said fluent medium includes means for introducing pressurized gas into said cavity and for retaining said gas captive therein under pressure thereby to maintain said elastic member resiliently compressed in uniformly distributed pressure contact with said medullary canal.

7. An endoprosthesis anchoring apparatus as defined in claim 6 characterized in the provision of means for releasing said pressurized gas from said cavity in said elastic member thereby releasing said endoprosthesis for unobstructed withdrawal from said medullary canal.

8. An endoprosthesis anchoring apparatus as defined in claim 1 characterized in that said elastic member comprises an elongated elastomeric bladder embracing the major portion of said stem and secured to axially spaced apart portions thereof in a fluid tight manner.

9. An endoprosthesis anchoring apparatus as defined in claim 1 characterized in that said stem is subdivided into a plurality of members longitudinally thereof including a first member between at least a member to either side thereof and each of which members extend axially beyond said elastic member and including means for detachably connecting a head thereto.

10. An endoprosthesis anchoring apparatus as defined in claim 9 characterized in the provision of fastener means normally detachably interconnecting said plurality of stem members; and said first member being withdrawable lengthwise of said stem when said fastener means is removed.

11. An endoprosthesis anchoring apparatus as defined in claim 10 characterized in the provision of means normally detachably interconnecting the remainder of said plurality of stem members, and said first member being withdrawable lengthwise of said stem upon detachment of said fastener means.

12. An endoprosthesis anchoring apparatus as defined in claim 10 characterized in that, after the withdrawal of said first stem member, the other members of said stem are collapsible toward one another to facilitate separation of said elastic member from a medullary canal and the removal of said endoprosthesis therefrom.

13. An endoprosthesis anchoring apparatus as defined in claim 9 characterized in that said first member is a blade the opposite sides of which converge toward one another from the thicker outer end thereof.

14. An endoprosthesis anchoring apparatus as defined in claim 9 characterized in that said members to either side of said first member are movably connected to one another adjacent the inner, thinner end of said first member.

15. An endoprosthesis anchoring apparatus as defined in claim 9 characterized in that said prosthesis includes a head having a threaded well mateable with the composite of threaded extensions on said first stem member and on the stem members to either side of said first stem member when said threaded extensions are in aligned side-by-side contact.

16. An endoprosthesis anchoring apparatus as defined in claim 15 characterized in the provision of puller means having a first portion securable to the outer end of said first stem member and a second portion engageable with the outer end of at least one of said stem members to either side of said first stem member and manipulatable to withdraw said first member from between said members to either side thereof.

17. An endoprosthesis anchoring apparatus as defined in claim 1 characterized in that said stem is formed with a radially opening groove encircling the outer end portion thereof; and said elastic member having a portion thereof shaped and sized to seat snugly in said groove; and the exterior of said elastic member radially opposite said groove having a close telescopic fit with the adjacent wall of a medullary canal when inserted therein.

18. An endoprosthesis anchoring apparatus as defined in claim 9 characterized in that said plurality of stem members are generally elliptical in cross section with the plane of said first stem member lying generally parallel with the major axis of said stem.

19. An endoprosthesis anchoring apparatus as defined in claim 1 characterized in that said elastic member comprises a thick-walled elastomeric bladder embracing said stem and having the opposite ends thereof in fluid tight contact with the adjacent end portions of said stem; and said bladder being chargeable with an initially fluent rigidly settable medium maintained pressurized while said medium takes a generally rigid set thereby to hold said bladder elastically pressed against the juxtaposed surface of a medullary canal.

20. That method of anchoring an endoprosthesis immovably in a medullary canal comprising:
providing an elongated rigid load bearing stem;
embracing said stem with an elongated elastomeric member; which is fluid impervious and has an internal cavity;
securing opposite end portions of said elastomeric member to a respective end of said stem;
inserting said stem and elastomeric member into the open end of a medullary canal; and
pressuring said elastomeric member inwardly of an outer wall thereof with a fluent material introduced under pressure into said internal cavity to expand said outer wall of the elastomeric member radially outwardly into pressurized contact with a juxtaposed surface of the medullary canal and continuously maintaining the outer wall of the elastomeric member compressed in resilient pressure contact with the medullary canal surface, said elastomeric member being effective to distribute elastic pressure substantially uniformly to the surface area of the medullary canal in contact therewith and conform to irregularities present in the juxtaposed surface portion of the medullary canal while said uniformly distributed elastic pressure applied continuously by the elastomeric member to the medullary canal is effective to anchor said endoprosthesis immovably therein.

21. That method defined in claim 20 characterized in the step of utilizing an elastomeric member having inner and outer walls constructed to provide a closed annular cavity therebetween; and charging said cavity with an initially fluent rigidly settable medium under a predetermined superatmospheric pressure and maintaining said pressure thereon while said fluent medium takes a rigid set thereby anchoring said prosthesis immovably against the surface of said medullary canal under uniformly distributed elastic pressure.

22. That method defined in claim 20 characterized in the step of pressurizing the inner side of said elastomeric member with an initially fluent rigidly settable medium maintained under a predetermined pressure while the same sets and selected for its friability when subjected to deliberately applied impact and shock forces imposed thereon to permit withdrawal of said endoprosthesis from a medullary canal.

23. That method defined in claim 20 characterized in the step of pressurizing the inner side of said elastomeric member with an initially fluent rigidly settable medium maintained under a predetermined pressure until the same sets into a rigid mass.

24. That method defined in claim 21 characterized in the step of pressing said elastomeric member against the surface of said medullary canal with a uniformly distributed pressure typically effective to foster and invigorate growth of the portion of the medullary canal opposed to and in contact with said elastomeric member thereby to augment the anchorage of said endoprosthesis thereto.

25. That method defined in claim 21 characterized in the step of precisely aligning a medullary canal, said endoprosthesis and an acetabular socket therefor before pressurizing said elastomeric member.

26. That method defined in claim 25 characterized in the step of pressurizing said elastomeric member with an initially fluent rigidly settable medium which takes a rigid set with said medullary canal, said endoprosthesis and said acetabular socket in precise alignment.

27. A pressurizable elastic endoprosthesis anchoring apparatus freely insertable into a medullary canal and thereafter immovably anchorable thereto comprising:
   a rigid main body including a load bearing stem supporting a head on one end thereof;
   tubular elastomeric means having at least one tubular outer wall embracing said stem with opposite end portions thereof secured to said stem in a fluid-tight manner to provide at least one closed annular cavity; and
   means for pressurizing said annular cavity to hold said at least one tubular outer wall pressed into resilient continuously maintained pressurized contact with the juxtaposed surface of a medullary canal to distribute elastic pressure substantially uniformly to the juxtaposed surface area of the medullary canal in contact therewith and to conform to irregularities present in said surface and to anchor said endoprosthesis immovably therein under said uniformly distributed elastic pressure continuously applied by the outer wall of said elastomeric means.

28. An endoprosthesis anchoring apparatus as defined in claim 27 characterized in that said annular cavity is charge with initially fluent medium which takes a rigid set and maintained pressurized to a predetermined pressure until said medium takes a rigid set.

29. An endoprosthesis anchoring apparatus as defined in claim 28 characterized in the provision of means for venting air from said cavity while charging the same with said fluent medium.

30. An endoprosthesis anchoring apparatus as defined in claim 27 characterized in that said annular cavity is charge with pressurized gas maintained permanently pressurized to a predetermined pressure.

31. An endoprosthesis anchoring apparatus as defined in claim 27 characterized in that said tubular elastomeric means includes a plurality of flexible concentric walls embracing said stem and cooperating therewith to form closed inner and outer cavities; and said outer cavity being substantially evacuated before insertion into a medullary canal.

32. An endoprosthesis anchoring apparatus as defined in claim 31 characterized in that said outer cavity is adapted to be filled with a captive quantity of gas pressurized to a predetermined pressure to hold the outermost wall of said tubular elastomeric means pressed resiliently and immovably against the surface of said medullary canal.

33. An endoprosthesis anchoring apparatus as defined in claim 31 characterized in that said outer cavity includes means for sealing the same closed filled with gas substantially at atmospheric pressure; and means for sealing said inner cavity closed with an initially fluent rigidly settable medium pressurized to a predetermined superatmospheric pressure thereby to pressurize the gas in said outer cavity and to hold the outer wall of said elastomeric means immovably anchored to the juxtaposed surface of a medullary canal under uniformly distributed predetermined pressure.

34. An endoprosthesis anchoring apparatus as defined in claim 30 characterized in that said inner cavity is charged with an initially fluent medium compounded to take a rigid set.

35. An endoprosthesis anchoring apparatus as defined in claim 27 characterized in that said elastomeric means comprises a pair of flexible concentric elastic walls loosely embracing said stem, the opposite ends of said walls being sealed to one another and to the respective adjacent ends of said stem and cooperating with said stem to provide a pair of independent inner and outer cavities; and passage means for introducing a pressurized medium into at least one of said cavities to hold the outermost one of said elastic walls pressed under substantially uniformly distributed pressure contact with the juxtaposed surface of a medullary canal.

36. An endoprosthesis anchoring apparatus as defined in claim 35 characterized in that said inner cavity is chargeable with an initially fluent rigidly settable medium maintained under pressure until it takes a rigid set thereby to hold the walls of said tubular elastomeric means pressed together with the outermost of said walls in uniformly distributed pressure contact with a medullary canal.

37. An endoprosthesis anchoring apparatus as defined in claim 35 characterized in that the outer one of said cavities includes a trapped quantity of gas at substantially atmospheric pressure after said endoprosthesis has been inserted into a medullary canal; and the inner one of said cavities being chargeable with a non-gaseous medium maintained under a predetermined superatmospheric pressure until said medium takes a rigid set and effective to compress the gas in said outer cavity to substantially the same pressure and thereby effective to press said outer elastic wall pressed immovably into conformity with the juxtaposed surface of a medullary canal.

* * * * *